US00PP35007P2

(12) United States Plant Patent
Hanes

(10) Patent No.: US PP35,007 P2
(45) Date of Patent: Feb. 28, 2023

(54) ***PELARGONIUM* PLANT NAMED 'PEQZ0100'**

(50) Latin Name: ***Pelargonium* interspecific**
Varietal Denomination: PEQZ0100

(71) Applicant: SYNGENTA CROP PROTECTION AG, Basel (CH)

(72) Inventor: Mitchell E. Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/949,568

(22) Filed: Sep. 21, 2022

(51) Int. Cl.
*A01H 5/02* (2018.01)
*A01H 6/42* (2018.01)

(52) U.S. Cl.
USPC ..... Plt./330
CPC ..... *A01H 6/425* (2018.05)

(58) Field of Classification Search
USPC ..... Plt./330
CPC ..... A01H 6/425; A01H 5/02
See application file for complete search history.

*Primary Examiner* — Keith O. Robinson
(74) *Attorney, Agent, or Firm* — Dale Skalla

(57) ABSTRACT

A new *Pelargonium* plant named 'PEQZ0100' particularly distinguished by vivid bright deep rose colored inflorescences with single florets and vivid purple spots on the petals, on a vigorous, mounding plant.

1 Drawing Sheet

Latin name of the genus and species of the plant claimed: *Pelargonium* interspecific.

Varietal denomination: 'PEQZ0100'.

BACKGROUND OF THE NEW PLANT

The present invention comprises a new *Pelargonium*, botanically known as *Pelargonium* interspecific, and hereinafter referred to by the variety name 'PEQZ0100'.

'PEQZ0100' is a product of a planned breeding program. The new cultivar 'PEQZ0100' has vivid bright deep rose colored inflorescences with single florets and vivid purple spots on the petals, on a vigorous, mounding plant.

'PEQZ0100' originates from a hybridization in a controlled breeding program made in July 2016 in a greenhouse in Gilroy, Calif. The female parent was an unpatented plant of *P.* x interspecific parentage identified as '11599-1V' with larger florets, and lighter green foliage when compared to 'PEQZ0100'.

The male parent of 'PEQZ0100' was an unpatented, proprietary plant of *P.* x *hortorum* parentage, identified as 'PEIB1012-1V' with more intense colored upper petals when compared to 'PEQZ0100'. The resultant seed was sown in December 2016.

'PEQZ0100' was selected as one flowering plant within the progeny of the stated cross in May 2017 in a greenhouse in Gilroy, Calif.

The first act of asexual reproduction of 'PEQZ0100' was accomplished when vegetative stem cuttings were propagated from the initial selection in June 2017 in a greenhouse in Gilroy, Calif.

BRIEF SUMMARY OF INVENTION

Horticultural examination of plants grown from cuttings of the plant initiated in July 2017 in Gilroy, Calif. and continuing thereafter, has demonstrated that the combination of characteristics as herein disclosed for 'PEQZ0100' are firmly fixed and are retained through successive generations of asexual reproduction.

'PEQZ0100' has not been observed under all possible environmental conditions. The phenotype may vary significantly with variations in environment such as temperature, light intensity, and day length.

A Plant Breeder's Right for this cultivar has not yet been applied for. 'PEQZ0100' has not been made publicly available prior to the effective filing date of this application, notwithstanding any disclosure that may have been made less than one year prior to the effective filing date of this application by the inventor or another who obtained 'PEQZ0100' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 1:
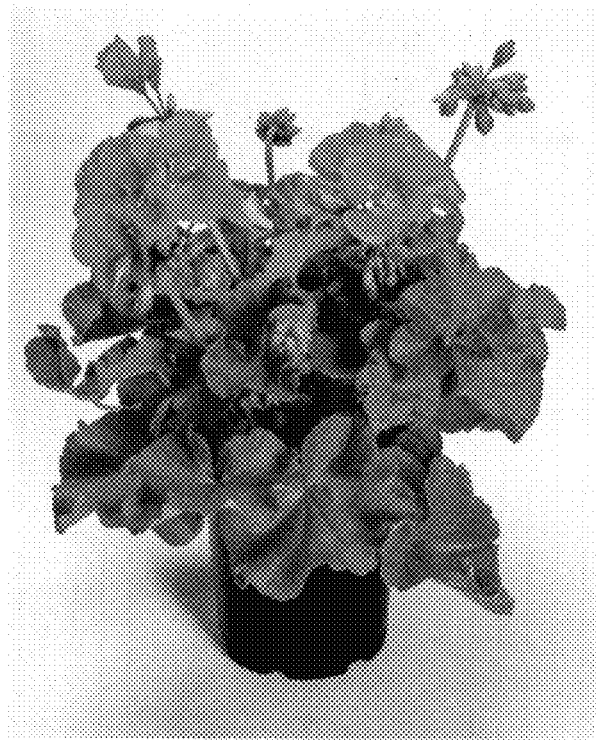
Figure 2:
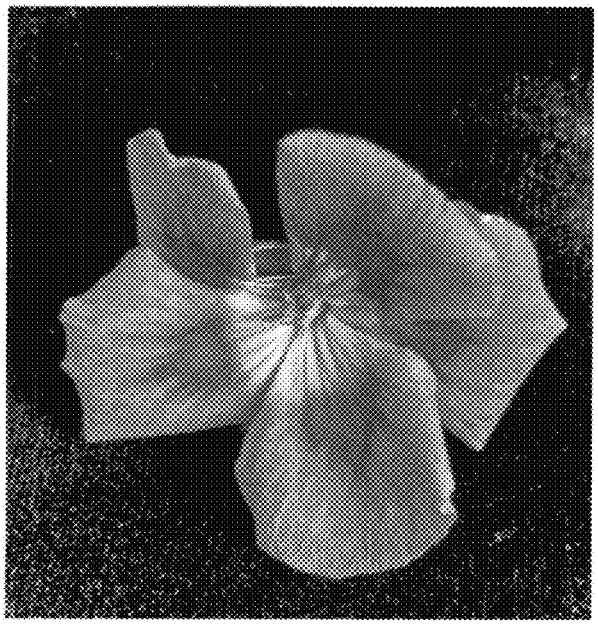

The accompanying photographic drawings show typical flower and foliage characteristics of 'PEQZ0100' with colors being as true as possible with an illustration of this type. The photographic drawings show in FIG. 1, one flowering plants of the new variety and in FIG. 2, a close-up of an inflorescence.

DETAILED BOTANICAL DESCRIPTION

The plant descriptions, measurements and photos were taken in Gilroy, Calif. in September 2022 under natural light. The plant was approximately 24 weeks old and was grown in a 30 cm pot, in a greenhouse trial.

Color references are made to The Royal Horticultural Society Colour Chart (R.H.S.) 2001.

TABLE 1

DIFFERENCES BETWEEN THE NEW VARIETY 'PEQZ0100' AND A MOST SIMILAR VARIETY

| | 'PEQZ0100' | 'PEQZ0017' (U.S. Plant Pat. No. 28,711) |
|---|---|---|
| Color upper side upper petal: | Dark pink RHS 67C with purplish red RHS N66A spot | Light pink, RHS 62B (with RHS 57B spot) |
| Pollen color: | Greyed-orange RHS N167B | Light orange RHS 25B |

Plant:

*Form, growth and habit.*—Semi-spreading and semi-upright growth habit.

*Plant height.*—20-24 cm.

*Plant height (inflorescence included).*—24-34 cm.

*Plant width.*—40-46 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Variegation.*—Absent.

*Immature leaf, color upper surface.*—Closest to RHS 138A.

*Immature leaf, lower surface.*—Closest to RHS 138B.

*Mature leaf, color upper surface.*—Closest to RHS 137B.

*Mature leaf, color lower surface.*—Closest to RHS 138B.

*Length.*—6-7 cm.

*Width.*—7.5-10 cm.

*Shape.*—Cordate.

*Base shape.*—Cordate.

*Sinus of mature leaf.*—Variable, very narrow to narrow on young mature leaf, more wode on older.

*Leaf base openness.*—Variable, some leaves almost closed, some leaves open or slightly open.

*Apex shape.*—Acute.

*Margin.*—Slightly dentate.

*Texture upper side.*—Hirsute.

*Texture lower side.*—Hirsute.

*Leaf zonation color.*—None.

*Color of veins, upper surface.*—RHS 137B, largely indistinct.

*Color of veins, lower surface.*—RHS 144A, becoming indistinct.

*Pattern of veining.*—Palmate.

*Petiole color.*—RHS 143B, slightly mottled close to RHS 176C.

*Petiole length.*—5-11 cm.

*Diameter of petiole.*—0.2 cm.

*Texture.*—Pilose, hirsute, glandular hairs.

Stem:

*Quantity of branches.*—5-10.

*Color of stem.*—Close to RHS 143C.

*Anthocyanin coloration of stem.*—No anthocyanin coloration present in stems.

*Length of stem.*—13-19 cm.

*Diameter.*—0.5-1 cm.

*Length of internodes.*—1-4 cm.

*Texture.*—Sparsely hirsute, pilose, glandular hairs.

Peduncle:

*Color of peduncle.*—RHS 144A.

*Length of peduncle.*—12-19.5 cm.

*Peduncle diameter.*—0.3-0.5 cm.

*Texture.*—Hirsute, glandular hairs.

*Anthocyanin coloration of peduncle.*—A slight anthocyanin coloration is visible under high solar radiation on middle third.

Pedicel:

*Color of pedicel.*—Basal part RHS 144A, not often, but you will see marks of RHS N199A and RHS 176A.

*Length of pedicel.*—3-3.5 cm.

*Diameter of pedicel.*—0.15-0.2 cm.

*Texture.*—Sparsely pilose, glandular hairs.

*Pedicel swelling.*—Swelling was not observed.

Bud (just before opening):

*Color.*—RHS 144A.

*Length.*—1.2-1.5 cm.

*Width.*—0.6-0.7 cm.

*Shape.*—Elliptical.

Inflorescence:

*Type.*—Umbel; semi-spherical or nearly semi- spherical.

*Lastingness of individual flowers.*—7-9 days at 18° C. temperature.

*Number of inflorescences per plant.*—6-12, with 5-12 immature umbels in various stages.

*Average total number of buds.*—65.

*Fragrance.*—None.

*Umbel diameter.*—8-10 cm.

*Umbel depth.*—5-7 cm.

Corolla:

*Form.*—Semi-double.

*Number of petals.*—5-7.

*Diameter of flower.*—4-5.5 cm.

*Depth of flower.*—1.5-2 cm.

*Side view shape.*—Concave.

*Color upper petals, upper surface.*—Tips of the petal start with RHS NN155C with middle spot containing RHS N66A and ending with RHS 67C.

*Color upper petals, lower surface.*—RHS NN155C at anthesis with RHS N66D to follow and with veins being RHS N66C.

*Length of upper petals.*—1.5-2.2 cm.

*Width of upper petals.*—2.1-2.6 cm.

*Color lower petals, upper surface.*—Tips of the petal start with RHS NN155C with middle spot containing RHS N66A and ending with RHS 67C.

*Color lower petals, lower surface.*—RHS NN155C at anthesis with RHS N66D to follow and with veins being RHS N66C whiter.

*Markings on upper petals.*—None.

*Markings on lower petals.*—May have veins of RHS N66A in white region.

*Length of lower petals.*—2.4-2.6 cm.

*Width of lower petals.*—1.8-2.2 cm, petaloids variably smaller smaller and with variable shape.

*Petal shape.*—Obovate to spathulate.

*Apex shape.*—Rounded.

*Margin.*—Entire.

*Base*.—Attenuate.
*Petal texture*.—Papillose on both surfaces.
Calyx:
*Number of sepals*.—5.
*Color of sepals*.—RHS 144A.
*Length of sepals*.—1-1.4 cm.
*Width of sepals*.—0.2-0.4 cm.
*Sepal shape*.—Lanceolate to linear.
*Apex shape*.—Acute.
*Margins*.—Mostly fused.
*Texture, upper surface*.—Glabrous.
*Lower surface*.—Glandular hairs, hirsute.
*Sepal flexing*.—Mostly unflexed sepals. The narrowest. sepals might flex moderately.
Reproductive organs:
Gynoecium:
*Pistil*.—RHS 145A.
*Length*.—0.8-0.9 cm.
*Style color*.—RHS 145A.
*Style length*.—0.4-0.5 cm.
*Stigma color*.—RHS 71C.
*Ovary color*.—RHS 144A.
*Ovary length*.—0.4-0.5 cm.
*Ovary diameter*.—0.2 cm.
Androecium:
*Number of stamens*.—6-9 with 1-5 staminoids.
*Color of filaments*.—RHS N155A with RHS 72D at the tip.
*Length filaments*.—0.5-0.6 cm.
*Anther color*.—RHS 171D.
*Length of anthers*.—0.3 cm.
*Color of pollen*.—RHS N167B.
*Pollen amount*.—Scarce.
*Fertility/seed set*.—Has not been determined to date.
*Disease/pest resistance*.—Has not been determined to date.

What is claimed is:

1. A new and distinct variety of *Pelargonium* plant named 'PEQZ0100' substantially as illustrated and described herein.

* * * * *